United States Patent
Hare

(10) Patent No.: US 10,500,525 B2
(45) Date of Patent: Dec. 10, 2019

(54) METHOD FOR PRODUCING AN EXTRACT FROM CANNABIS PLANT MATTER

(71) Applicant: Curtis Hare, Marlette, MI (US)

(72) Inventor: Curtis Hare, Marlette, MI (US)

( * ) Notice: Subject to any disclaimer, the term of this patent is extended or adjusted under 35 U.S.C. 154(b) by 341 days.

(21) Appl. No.: 15/679,608

(22) Filed: Aug. 17, 2017

(65) Prior Publication Data

US 2019/0054394 A1    Feb. 21, 2019

(51) Int. Cl.
| | |
|---|---|
| *A61K 36/00* | (2006.01) |
| *B01D 11/04* | (2006.01) |
| *C11B 1/10* | (2006.01) |
| *A61K 31/352* | (2006.01) |
| *A61K 36/18* | (2006.01) |

(52) U.S. Cl.
CPC ............ *B01D 11/04* (2013.01); *A61K 31/352* (2013.01); *A61K 36/18* (2013.01); *C11B 1/10* (2013.01); *A61K 2236/35* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 7,608,729 B2 | 10/2009 | Winsness |
| 8,337,908 B2 | 12/2012 | Ebell |
| 8,778,433 B2 | 7/2014 | Lee |
| 8,895,078 B2 | 11/2014 | Mueller |
| 2016/0325288 A1 | 11/2016 | Bates |
| 2017/0020943 A1* | 1/2017 | Raderman ............ A61K 36/185 |

* cited by examiner

*Primary Examiner* — Michael V Meller
(74) *Attorney, Agent, or Firm* — Andrew Morabito

(57) ABSTRACT

The invention is a process of extracting Δ9-THC from *cannabis*, the method comprising, gathering a quantity of plant parts, shredding the quantity of plant parts into a particulate matter, heating the particulate matter at a temperature, wherein the particulate undergoes a decarboxylation process converting a quantity of the THCA-A within the particulate matter to a quantity of Δ9-THC, combining the decarboxylated particulate matter with a quantity of a predetermined liquid within a sealed pressurized container, wherein the pressure ranges from 10 to 15 PSI for a predetermined time period, wherein the quantity of the Δ9-THC is extracted from the decarboxylated particulate matter and the quantity of Δ9-THC is chemically bonded with the liquid, and a Δ9-THC liquid is formed, sifting the particulate matter from the Δ9-THC liquid, and cooling the Δ9-THC.

3 Claims, 1 Drawing Sheet

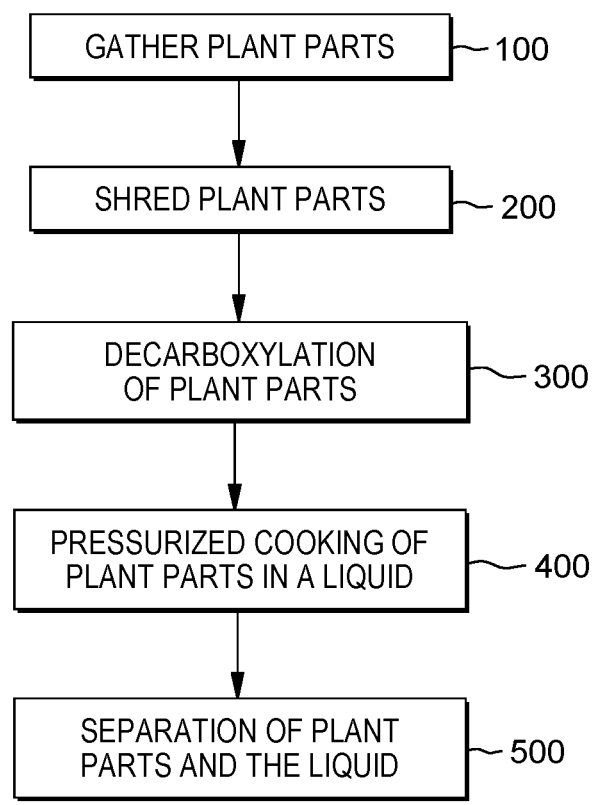

METHOD FOR PRODUCING AN EXTRACT FROM CANNABIS PLANT MATTER

BACKGROUND

The present invention relates to a process for extracting tetrahydrocannabinol from plant parts, and further comprising the use of a pressurized environment to maximize the chemical bonding of the tetrahydrocannabinol with a liquid.

Cannabis contains tetrahydrocannabinol carboxylic acid (THC-COOH); this substance is also referred to as THC acid, Δ9-THC acid, THCA-A, or THCA. THC acid may be converted into the psychoactive substance Tetrahydrocannabinol (THC), also known as ($\Delta^9$-THC) through processes that decarboxylate the THC acid. Decarboxylation is a chemical reaction that converts an acid to a phenol and releases carbon-dioxide ($CO2$); a carbon atom is removed from a carbon chain.

Other processes have been used to extract Δ9-THC from *cannabis* in uncontrolled ways, some of these processes use toxic materials and others do not; frequently such processes attempt to produce a final product in a single uncontrolled crude step.

Examples of such processes include the use of butane, a toxic solvent, to make the *cannabis* "red oil" commonly called hash oil. *Cannabis* is saturated in butane, the butane reduces the *cannabis* into an oil that is separated from the plant material, the butane evaporates continuously during the process of reduction; a paper filter is used to separate the oil from plant material. The author also recommends a secondary process of mixing the oil with isopropyl alcohol, then evaporating the isopropyl alcohol overnight by letting it sit. The author of this reference believes that the isopropyl alcohol reduces the photosensitivity of THC contained within the oil. The process disclosed has no scientific controls, and shows disregard for laws relating to treating *cannabis* as a controlled substance or preparation of food products. The disclosure is provided as an example of uncontrolled methods that are available to the public.

In contrast, uncontrolled crude processes that use no toxic chemicals include simply baking *cannabis* into cookies or bread, or making a tea by steeping *cannabis* in hot water. *Cannabis* infused dairy butter can be made by melting dairy butter in a pot, adding *cannabis* and cooking the mixture for a period of time, up to 24 hours.

Smoking, in the form of a cigarette or pipe, is the most frequently used uncontrolled process for decarboxylating *cannabis*.

The processes discussed above that rely on temperature simply use temperature yet do not control temperature; if the temperature is too low decarboxylation will be incomplete, if temperatures are too high decarboxylated substances within *cannabis* will be lost to evaporation. Temperature control is therefore characteristic of a process that relies on temperature to decarboxylate. This is why the "uncontrolled" processes reviewed above that rely on temperature are truly uncontrolled.

Recently, with the legalization of medical *cannabis* in 14 states, various edible *cannabis* products have become available; such products include cookies, biscuits, cooking oil, and dairy butter. These products are made without scientific controls by small producers because pharmaceutical companies do not produce edible *cannabis* products. Products like cookies or biscuits are eaten as is; products like cooking oil or dairy butter are usually added or cooked into other foods. Each one of these individual edible products have limitations the most significant one is uncontrolled dosage, cookies or biscuits contain *cannabis* fiber that often makes them green in color, and dairy products such as dairy butter spoil at room temperature.

As a general rule, all the plant parts of *Cannabis sativa* L. with the exception of the seeds may contain cannabinoids. The highest cannabinoid concentrations are found in the floral bracts and fruit stalks. The leaves have a low content of cannabinoids as a function of leaf age, while the stalk and particularly the root exhibit clearly lower cannabinoid contents. Typically, the concentration of the cannabinoids in the leaf, stalk and roots ranges between 2% and 7%. It is desirable to extract the cannabinoids from the floral bracts and fruit stalks and the rest of the plant is viewed as unusable or waste product for cannabinoid production. The above discussed methods are not, or typically do not employ the parts of the plan which contain the lower percentages of Δ9-THC and are viewed as waste material, but still provide the benefits that the rest of the plant provides.

Benefits such as the many of the therapeutical effects handed down are coming to be confirmed in clinical research. At present, the pharmacological use of *cannabis* active principles is of importance essentially in the following indications: the appetite stimulating effect, in particular in the case of AIDS-related afflictions accompanied by cachexia and wasting syndrome, the antiemetic action for inhibiting nausea and vomiting, particularly in connection with chemotherapy under administration of cytostatic agents, the reduction of muscle cramps and spasms in multiple sclerosis and traverse lesions of the cord with paraplegia, pain and migraine treatment—in chronic pain therapy also complementarily with opioid treatment, lowering intra-ocular pressure in glaucoma, mood improvement, and in particular cannabidiol as an anti-epileptic, as well as various other diseases such as anxiety disorders, post-traumatic stress disorder, psychosis, epilepsy, dystonia, diabetes, cancer, inflammatory diseases, and skin diseases.

A process for the production of a food grade intermediate product containing a known amount of Δ9-THC which is gathered from the waste or by product of the plant in controlled ways is the focus of the invention disclosed below.

SUMMARY

The invention relates to the process for extracting Δ9-THC from *cannabis*, the process comprising: gathering a predetermined quantity of plant parts; shredding the predetermined quantity of plant parts into a particulate matter of predetermined size; heating under a supercritical temperature the particulate matter at a temperature in a range of 225 to 245 degrees Fahrenheit, wherein the particulate undergoes a decarboxylation process converting a quantity of the THCA-A within the particulate matter to a quantity of Δ9-THC; combining the decarboxylated particulate matter with a quantity of a predetermined liquid within a sealed pressurized container, wherein the pressure ranges from 10 to 15 PSI for a predetermined time period, wherein the quantity of the Δ9-THC is extracted from the decarboxylated particulate matter and the quantity of Δ9-THC is chemically bonded with the liquid, and a Δ9-THC liquid is formed; sifting the particulate matter from the Δ9-THC liquid; and cooling the Δ9-THC liquid at a temperature in the range of 20 to 40 degrees Fahrenheit.

The invention relates to a further embodiment of a process for extracting Δ9-THC from *cannabis*, the method comprising: shredding the predetermined quantity of plant parts which contain THCA-A into a particulate matter of predetermined size of approximately one inch in length; heating particulate matter at a temperature in a range of 225 to 245 degrees Fahrenheit, wherein the particulate matter undergoes a decarboxylation process, wherein a decarboxylated particulate matter is created that container a predetermined amount of Δ9-THC; combining the decarboxylated particulate matter with a quantity of liquid wherein a mixture is created within a substantially sealed heated pressurized container, wherein the pressure ranges from 10 to 15 PSI and the temperature ranges from 310 to 360 degrees Fahrenheit, for a predetermined time, the Δ9-THC is released from the decarboxylated particulate matter and is chemically bonded to the quantity of liquid, and a Δ9-THC liquid is formed;

BRIEF DESCRIPTION OF SEVERAL VIEWS OF THE DRAWINGS

FIG. 1 depicts a block diagram of the extraction process, in accordance with one embodiment of the present invention.

DETAILED DESCRIPTION

As will be appreciated by one skilled in the art, aspects of the present invention may be embodied as a system, method, or process. Accordingly, aspects of the present invention may take the form of an entirely hardware embodiment, an entirely process embodiments, or a combination of the two.

The invention relates to the controlled decarboxylation of raw *cannabis*. First shredding the plant parts to a predetermined size. Then curing the plant parts to decarboxylate the raw *cannabis* into decarboxylated *cannabis*. Then pressurizing the decarboxylated *cannabis* with a liquid and boiling the mixture without vaporizing the decarboxylated *cannabis*, thereby chemically bonding the Tetrahydrocannabinol ("Δ9-THC") with the liquid. This process may be employed with various other vegetation and plants to extract specific chemicals and compounds through the decarboxylation process.

The process provides controlled decarboxylation of raw *cannabis* into decarboxylated *cannabis*, then bonds the decarboxylated *cannabis* with a liquid. The term decarboxylated *cannabis* is a general term for the Δ9-THC which is present in the *cannabis* after the decarboxylation process that may also contain related substances that include, yet are not limited to cannabinoids, cannabiniols, cannbidiols, and cannabigerol. Δ9-THC contained or used in products or processes consistent with this invention may also contain related substances that include, yet are not limited to cannabinoids, cannabiniols, cannbidiols, and cannabigerol.

In raw *cannabis* tetrahydrocannabinolic acid ("THCA-A") content of 5% to 25% by volume are typical. The THCA-A is converted to Δ9-THC during the decarboxylation In a perfect environment the THCA-A is 100% concerted to Δ9-THC. This perfect reaction however is difficult or nearly impossible to accomplish especially in the portions of the plant which is substantially less THCA-A. The steps performed in this process provide a process in which a user can gather a higher yield of Δ9-THC from the plant parts with the lower THCA-A content. In this instance some of the THCA-A contained within the raw *cannabis* will simply not be converted to Δ9-THC; the advantage of this approach is that the process will produce essentially the same output even when the lower THCA-A content of the raw *cannabis* plant part inputs than with previous processes.

Referring to the accompanying FIGURES, there is illustrated a system for processing hemp stalks sticks and leaves, flowers, pistils, seeds, and roots of the male and female plants (hereinafter "plant parts"). The system is configurable to extract the Δ9-THC and other substances from the plant parts.

The system commences with a gathering stage 100 for receiving the plant parts. The plans parts may include the roots, leaves, stalks, seeds, nodes, calyx, pistils, colas, of the male and female plants. In some embodiments, the whole hemp plant is received without the buds or flowering portions of the plant that are usually gathered for the Δ9-THC. The plant is received in pieces that are of a predetermined size. The hemp plant may be received in various sizes and pieces. The size of the plant is adjustable and is typically in smaller portions than the entire plant, as the portions of the plant with the highest concentration of Δ9-THC is typically removed before being is employed. Thus, the plants may come in the form of the entire plant from roots to pistils, or may be sections or segments of the plant that were cut or removed during the gathering of the buds or flowering portions of the plant. This process is a method to extract the Δ9-THC from the plant parts of the *cannabis* plant so the condition and state of the plant parts may vary. The plant parts that are gathered may have varying degrees of internal moisture levels. The plant parts may be pre dryed or cured and have a moisture level of approximately 10%, but may range up to 30%. In additional embodiments, the plant parts may have a moisture level of approximately 40%

After the gathering stage, the plant parts are transferred to a shredding stage 200 which performs the cutting of the plant parts into smaller and more evenly sized plant parts. The shredding step may also refer to crushing, smashing, grinding, or the equivalent processes. The shredding stage comprises a shredding station which produces the cut plant parts to have an average piece dimension in a prescribed piece range. The shredding stage may employ various industrial or home use shredding or processing machines, such as an electric chip shredder. In some embodiments, the plant parts may be cut by hand using pruning shears or the like. Preferably between one inches and two inches. In additional embodiments, the cut plant parts may range from one half inches to four inches and provide comparable results to the preferred prescribed piece range. The cut plant parts range is analogous to mulch.

After the shredding stage, the plant parts are transferred to the baking stage which performs the drying of the plant parts and the initiation of the decarbonxylation process of the plant parts 300. The decarbonxylation of the plant parts removes the carboxyl group from the THCA-A found in the plant parts, to give the creation of the Δ9-THC. The baking stage uses a high temperature oven operating at a temperature of 220 degrees Fahrenheit to 250 degrees Fahrenheit (operating at 235 degrees Fahrenheit is preferred) to cook the plant parts. The desired quantity of plant parts for the preferred embodiment is 12 ounces of shredded plant parts. In additional embodiments, additional temperatures may be used based on the amount of plant parts in the oven, the moisture content of the plant parts, or the size of the oven used. The plant parts are placed in the oven for a time ranging from 30 minutes to 40 minutes (preferably 35 minutes). In some instance where the moisture content or the quantity of plant parts is too high such that the plant parts are not properly baked, the plant parts remain in the oven for an extended period of time.

The cured plant parts are then transferred to a pressurized cooking vessel to extract the Δ9-THC from the plant parts by cooking the plant parts in liquid 400. Once the plant parts are placed in the pressurized cooking vessel a predetermined amount of liquid is added to the container. In one embodiment, the twelve ounces of cured plant parts are placed in a sixteen-quart pressurized cooking vessel and four quarts of water are added to the pressurized cooking vessel. In additional embodiments, the amount of cured plant parts may be adjusted based on the size and capacity of the pressurized cooking vessel. In various embodiments, the water may be replaced with or mixed with various butters, creams, oils, or other liquids.

The pressurized cooking vessel is then sealed with the combination enclosed and the predetermined pressure setting and temperature settings are selected. The pressure within the pressurized cooking vessel is between 10 pounds per square inch (PSI) and 20 PSI (with the preferred pressure being 12 PSI). A higher or lower pressure may be employed depending on, the amount of plant parts, the amount of liquid within the vessel, or the type of liquid within the cooking vessel. Within the environment, the liquid is brought to a temperature above the ambient boiling point of the specific liquid, and the increased pressure assists in raising this boiling point. This environment increases release of the Δ9-THC from the plant parts, and also increases the Δ9-THC ability to chemically bonding with the liquid. Thus, increasing the concentration of the Δ9-THC in the liquid. For example, if water is used as the liquid a temperature of approximately 230 degrees Fahrenheit can be reached within an environment of 12 PSI. Due to this increased pressure and thus increased boiling point, the process is able to efficiently reach optimal temperatures which the various liquids break down and are able to bond with the now freed Δ9-THC.

Δ9-THC has a boiling point of approximately 314 degrees Fahrenheit and a vaporization temperature of 350 degrees Fahrenheit. An essential concept of this invention is the pressurized environment of the pressured cooking vessel, to allow the liquid, that under ambient temperatures is not able to reach the vaporization temperature of the Δ9-THC, to now be reached. When the Δ9-THC and the liquid are able to both reach this high temperature in a sealed environment, there is an increase in the ability for the now freed Δ9-THC to chemically bond with the liquid. In instances where, the liquid has a boiling point of approximately that of the Δ9-THC, the pressurized environment drastically reduces the time needed for the chemical bonding to occur.

Once the pressure within the vessel is reached, the contents remain within the pressured vessel for a time of approximately 3 hours. This time again can be adjusted based on the volume of the vessel and the ratio of plant parts to liquid. Due to pressurization of the vessel, and the temperature approximate to the vaporization temperature of the Δ9-THC is vapor is not lost because of the sealed environment, and is constantly circulated within the liquid to allow increased instances where the Δ9-THC can chemically bond with the liquid without being lost to an open or ventilated environment.

This method of pressurizing and heating the plant parts in the liquid unbind the Δ9-THC from the plant parts and the Δ9-THC is free to associate, and the liquid and the Δ9-THC chemically bond to one another in the high temperature high pressure environment. This high temperature high pressure release of the Δ9-THC from the plant parts is a unique aspect of the invention, as the high pressure allows a higher percentage of the Δ9-THC to be freed from the plant plants and allow to chemically bond with the liquid within the pressurized cooking vessel.

Based on the specific type of plant parts, the time and pressure may be adjusted to accommodate a desired heat and pressure to provide the most efficient unbinding of the Δ9-THC or other desired chemical from the plant parts. Some known substances which are also shown to be freed from the plant parts are cannabiniols and cannabinoids.

It is noted that boiling points, and vaporization temperatures of materials used in this process vary with ambient pressure and that specific temperatures referenced may vary upon ambient pressure; critical temperatures may therefore vary based on environmental pressures that can vary based on elevation, pressurized environments or even contaminants.

The contents of the vessel are cooled, and the Δ9-THC and/or associated compounds are bonded to the liquid. After the contents of the vessel are cooled, the contents are separated in the separation stage. The separation stage removes the unbonded oil that has mixed with the added liquid and the plant parts are separated from this mixture. Various types of separation devices and systems may be employed such as gravity separators, centrifuge or settling tanks, a sealed centrifuge, or the like can be employed by the system. This process may be repeated several times.

After the plant parts are separated 500 from the liquid through the use of strainer or other hardware that can separate the liquid from the solid; the liquid is then placed in a refrigerated environment to allow the Δ9-THC infused liquid to settle. In some embodiments, a centrifugal separator is used. In additional embodiments, a gravity separator is used. The waste plant parts can be used for to various types of animal feed, bedding, or filler material for various industries.

While a single embodiment is shown where the desired amount of THCA-A is converted to Δ9-THC, and then is bonded with the liquid. The ability to reduce or increase the potency of the final product can be accomplished at various stages of the process. First, increasing the amount of raw *cannabis* for the decarboxylation. Second, decreasing the amount of Δ9-THC which is added to the liquid in the vessel. Third, is by adjusting the type of liquid or the quantity of the liquid. A cup of water can chemically bond with a predetermined amount of Δ9-THC, producing a set potency, which four cups of water with the same amount of Δ9-THC will create a lower potency final product. A similar adjust can be made with the type of liquid as the chemical bonding ability varies from water, to butter, to various oils. In one example twelve (12) ounces of plant parts were processed and produced a final product that contained approximately 816.5 mg of Δ9-THC and only 54 mg of THCA, resulting in a final product that had 93.8% of active Δ9-THC in the final product out of the 871 cannabinoids present.

A significant aspect of this invention is the transformation of a controlled amount of raw *cannabis* into decarboxylated *cannabis* consistent with this disclosure. The overall process also bonds the Δ9-THC to a lipid; the lipid is then manufactured into a foodstuff base material containing a controlled amount of Δ9-THC per unit volume of the foodstuff base material.

Aspects of the present invention are described herein with reference to flowchart illustrations and/or block diagrams of process according to embodiments of the invention. It will be understood that each block of the flowchart illustrations and/or block diagrams, and combinations of blocks in the flowchart illustrations and/or block diagrams, can be implemented by computer readable program instructions. The flowchart and block diagrams in the FIGURE illustrate the architecture, functionality, and operation of possible implementations of the process according to various embodiments of the present invention. In this regard, each block in the flowchart or block diagrams may represent a step or portion of the process. In some alternative implementations, the functions noted in the block may occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Since various modifications can be made in the invention as herein above described, and many apparently widely different embodiments of same made, it is intended that all matter contained in the accompanying specification shall be interpreted as illustrative only and not in a limiting sense.

What is claimed is:

1. A process for extracting Delta 9-tetrahydrocannabinol from *cannabis*, the method consisting essentially of:
    a) shredding a predetermined quantity of *cannabis* which contains delta 9-Tetrahydrocannabinolic acid A into *cannabis* of about one inch in length;
    b) heating the *cannabis* at a temperature in a range of 225° F. to 245° F., wherein the *cannabis* undergoes a decarboxylation process, wherein a decarboxylated *cannabis* is created that contains a predetermined amount of Delta 9-tetrahydrocannabinol;
    c) combining the decarboxylated *cannabis* with a quantity of water to create an aqueous decarboxylated *cannabis*;
    d) pressurizing the aqueous decarboxylated *cannabis* within a substantially sealed heated pressurized container, wherein the pressure ranges from 10 PSI to 15 PSI and the temperature ranges from 310° F. to 360° F., for a predetermined time, wherein the Delta 9-tetrahydrocannabinol is released from the aqueous decarboxylated *cannabis* and is chemically bonded to the water, and an aqueous Delta 9-tetrahydrocannabinol is formed;
    e) sifting the aqueous Delta 9-tetrahydrocannabinol from the aqueous decarboxylated *cannabis*; and
    f) cooling the aqueous Delta 9-tetrahydrocannabinol at a temperature in the range of 20° F. to 40° F.

2. The process of claim 1, wherein in step d), the predetermined time is about 3 hours.

3. The process of claim 1, wherein the step of sifting is performed by a gravity separator.

* * * * *